(12) United States Patent
Ortiz et al.

(10) Patent No.: US 11,253,190 B2
(45) Date of Patent: Feb. 22, 2022

(54) DEVICES WITH REDUCED MICROFLUIDIC VOLUME BETWEEN SENSORS AND SWEAT GLANDS

(71) Applicants: University Of Cincinnati, Cincinnati, OH (US); Eccrine Systems, Inc., Cincinnati, OH (US)

(72) Inventors: Mark S. Ortiz, Milford, OH (US); Kyle N. Stewart, Cincinnati, OH (US); Robert Roth, Cincinnati, OH (US); Jason Charles Heikenfeld, Cincinnati, OH (US)

(73) Assignees: University of Cincinnati, Cincinnati, OH (US); Eccrine Systems, Inc., Cincinnati, OH (US)

( * ) Notice: Subject to any disclaimer, the term of this patent is extended or adjusted under 35 U.S.C. 154(b) by 485 days.

(21) Appl. No.: 16/310,551

(22) PCT Filed: Jul. 3, 2017

(86) PCT No.: PCT/US2017/040588
§ 371 (c)(1),
(2) Date: Dec. 17, 2018

(87) PCT Pub. No.: WO2018/006087
PCT Pub. Date: Jan. 4, 2018

(65) Prior Publication Data
US 2019/0175094 A1    Jun. 13, 2019

Related U.S. Application Data (60) Provisional application No. 62/357,643, filed on Jul. 1, 2016.

(51) Int. Cl.
*A61B 5/145* (2006.01)
*A61B 5/00* (2006.01)
*A61B 10/00* (2006.01)

(52) U.S. Cl.
CPC ........ *A61B 5/4266* (2013.01); *A61B 5/14517* (2013.01); *A61B 5/14546* (2013.01);
(Continued)

(58) Field of Classification Search
CPC ... A61B 5/145; A61B 5/1451; A61B 5/14514; A61B 5/14517; A61B 5/14521;
(Continued)

(56) References Cited

U.S. PATENT DOCUMENTS 4,190,060 A   2/1980 Greenleaf et al.
4,365,637 A   12/1982 Johnson
(Continued)

FOREIGN PATENT DOCUMENTS

CA   2869469 A1   10/2013
CN   1874720 A    12/2006
(Continued)

OTHER PUBLICATIONS

Buono, M. et al., "Cholinergic sensitivity of the eccrine sweat gland in trained and untrained men," 1992, J. Derm. Sci. 4, 33-37.
(Continued)

*Primary Examiner* — Eric F Winakur
(74) *Attorney, Agent, or Firm* — Wood Herron & Evans LLP (57) ABSTRACT

A sweat sampling and sensing device for sensing sweat on skin includes an analyte-specific sensor for sensing a first analyte in sweat; a sweat collector placed on or adjacent to skin with a plurality of pores or pathways for entry of sweat from skin into said sweat collector, said sweat collector at least partly defining a sweat volume between said analyte-specific sensor and the skin; and a pressure element capable of holding said sweat collector against the skin with a pressure and reducing the sweat volume between said sweat collector and the skin.

19 Claims, 6 Drawing Sheets

(52) U.S. Cl.
CPC .......... *A61B 5/6831* (2013.01); *A61B 5/6832* (2013.01); *A61B 5/6833* (2013.01); *A61B 5/6834* (2013.01); *A61B 5/6838* (2013.01); *A61B 5/6843* (2013.01); *A61B 10/0045* (2013.01); *A61B 10/0064* (2013.01)

(58) Field of Classification Search
CPC . A61B 5/14532; A61B 5/14546; A61B 5/683; A61B 5/6832; A61B 5/6834; A61B 5/6831
See application file for complete search history.

(56) References Cited

U.S. PATENT DOCUMENTS

| | | | |
|---|---|---|---|
| 4,542,751 A | 9/1985 | Webster et al. | |
| 4,756,314 A | 7/1988 | Eckenhoff et al. | |
| 4,820,263 A | 4/1989 | Spevak et al. | |
| 5,036,861 A | 8/1991 | Sembrowich et al. | |
| 5,050,604 A | 9/1991 | Reshef et al. | |
| 5,140,985 A | 8/1992 | Schroeder et al. | |
| 5,246,003 A | 9/1993 | DeLonzor | |
| 5,438,984 A | 8/1995 | Schoendorfer | |
| 5,480,651 A | 1/1996 | Callaway | |
| 5,507,286 A | 4/1996 | Solenberger | |
| 5,556,789 A | 9/1996 | Goerlach-Graw et al. | |
| 5,814,599 A | 9/1998 | Mitragotri et al. | |
| 5,944,662 A | 8/1999 | Schoendorfer | |
| 6,132,975 A | 10/2000 | Kanan et al. | |
| 6,198,953 B1 | 3/2001 | Webster et al. | |
| 6,256,533 B1 | 7/2001 | Yuzhakov et al. | |
| 6,269,265 B1 | 7/2001 | Anderson | |
| 6,299,578 B1 | 10/2001 | Kumik et al. | |
| 6,592,529 B2 | 7/2003 | Marett | |
| 6,666,821 B2 | 12/2003 | Keimel | |
| 7,190,986 B1 | 3/2007 | Hannula et al. | |
| 7,219,534 B2 | 5/2007 | Campbell | |
| 7,378,054 B2 | 5/2008 | Karmali | |
| 7,383,072 B2 | 6/2008 | Edmonson et al. | |
| 7,384,396 B2 | 6/2008 | Samuels et al. | |
| 7,749,445 B2 | 7/2010 | Masters | |
| 7,813,780 B2 | 10/2010 | Shah et al. | |
| 7,842,234 B2 | 11/2010 | Lauks et al. | |
| 7,959,791 B2 | 6/2011 | Kjaer et al. | |
| 8,125,539 B2 | 2/2012 | Takashima | |
| 8,128,889 B2 | 3/2012 | Fujimoto et al. | |
| 8,252,248 B2 | 8/2012 | Kramer | |
| 8,391,946 B2 | 3/2013 | Sugenoya et al. | |
| 8,565,850 B2 | 10/2013 | Martinsen et al. | |
| 8,593,287 B2 | 11/2013 | Hayter et al. | |
| 8,617,067 B2 | 12/2013 | Jain et al. | |
| 9,133,024 B2 | 9/2015 | Phan et al. | |
| 10,485,460 B2 | 11/2019 | Sonner et al. | |
| 2002/0091312 A1 | 7/2002 | Berner et al. | |
| 2003/0135100 A1 | 7/2003 | Kim et al. | |
| 2003/0191376 A1 | 10/2003 | Samuels et al. | |
| 2003/0201194 A1 | 10/2003 | Heller et al. | |
| 2004/0249310 A1 | 12/2004 | Shartle et al. | |
| 2004/0267189 A1 | 12/2004 | Mavor et al. | |
| 2005/0069925 A1 | 3/2005 | Ford et al. | |
| 2005/0096520 A1 | 5/2005 | Maekawa et al. | |
| 2005/0106713 A1 | 5/2005 | Phan et al. | |
| 2005/0177035 A1 | 8/2005 | Botvinick et al. | |
| 2005/0192528 A1 | 9/2005 | Tapper | |
| 2005/0197554 A1 | 9/2005 | Polcha | |
| 2006/0004271 A1 | 1/2006 | Peyser et al. | |
| 2006/0062852 A1 | 3/2006 | Holmes | |
| 2006/0127964 A1 | 6/2006 | Ford et al. | |
| 2006/0253011 A1 | 11/2006 | Edmonson et al. | |
| 2006/0254341 A1 | 11/2006 | Campbell | |
| 2007/0027383 A1 | 2/2007 | Peyser et al. | |
| 2007/0032731 A1 | 2/2007 | Lovejoy et al. | |
| 2007/0179371 A1 | 8/2007 | Peyser et al. | |
| 2008/0015494 A1 | 1/2008 | Santini et al. | |
| 2008/0045816 A1 | 2/2008 | Jang et al. | |
| 2008/0154179 A1 | 6/2008 | Cantor et al. | |
| 2008/0286349 A1 | 11/2008 | Nomoto et al. | |
| 2008/0306362 A1 | 12/2008 | Davis | |
| 2009/0076345 A1 | 3/2009 | Manicka et al. | |
| 2009/0204008 A1 | 8/2009 | Beilin | |
| 2009/0270704 A1 | 10/2009 | Peyser et al. | |
| 2010/0044224 A1 | 2/2010 | Kataky | |
| 2010/0063372 A1 | 3/2010 | Potts et al. | |
| 2010/0130843 A1 | 5/2010 | Caceres Galvez et al. | |
| 2010/0132485 A1 | 6/2010 | Erez et al. | |
| 2010/0179403 A1 | 7/2010 | Martinsen et al. | |
| 2010/0198521 A1 | 8/2010 | Haick | |
| 2010/0234712 A1 | 9/2010 | Sugenoya et al. | |
| 2011/0079521 A1 | 4/2011 | Revol-Cavalier | |
| 2011/0118656 A1 | 5/2011 | Eckhoff et al. | |
| 2011/0178380 A1 | 7/2011 | Chowdhury | |
| 2011/0196283 A1 | 8/2011 | Imran et al. | |
| 2011/0208458 A1 | 8/2011 | Pinter et al. | |
| 2011/0275918 A1 | 11/2011 | Yamashita et al. | |
| 2012/0004570 A1 | 1/2012 | Shimizu et al. | |
| 2012/0028283 A1 | 2/2012 | Hoss et al. | |
| 2012/0123220 A1 | 5/2012 | Iyer et al. | |
| 2012/0150072 A1 | 6/2012 | Revol-Cavalier et al. | |
| 2012/0165626 A1 | 6/2012 | Irina et al. | |
| 2012/0209226 A1 | 8/2012 | Simmons et al. | |
| 2012/0229661 A1 | 9/2012 | Sekiguchi et al. | |
| 2012/0271125 A1 | 10/2012 | Bernstein et al. | |
| 2012/0277697 A1 | 11/2012 | Haghgooie et al. | |
| 2012/0285829 A1 | 11/2012 | Mount et al. | |
| 2012/0317430 A1 | 12/2012 | Rahman et al. | |
| 2012/0323097 A9 | 12/2012 | Chowdhury | |
| 2013/0006079 A1 | 1/2013 | Feldman et al. | |
| 2013/0010108 A1 | 1/2013 | Hashizume et al. | |
| 2013/0013028 A1 | 1/2013 | Kriksunov et al. | |
| 2013/0053668 A1 | 2/2013 | Lin | |
| 2013/0053817 A1 | 2/2013 | Yun | |
| 2013/0079605 A1 | 3/2013 | Bandaru et al. | |
| 2013/0099937 A1 | 4/2013 | Azimi | |
| 2013/0108667 A1 | 5/2013 | Soikum et al. | |
| 2013/0123595 A1 | 5/2013 | Currie et al. | |
| 2013/0183399 A1 | 7/2013 | Blow et al. | |
| 2013/0197333 A1 | 8/2013 | Petisce | |
| 2013/0245388 A1 | 9/2013 | Rafferty et al. | |
| 2013/0306491 A1 | 11/2013 | Briman et al. | |
| 2013/0317333 A1 | 11/2013 | Yang et al. | |
| 2014/0012114 A1 | 1/2014 | Zevenbergen et al. | |
| 2014/0025000 A1 | 1/2014 | Currie et al. | |
| 2014/0046423 A1 | 2/2014 | Rajguru | |
| 2014/0066726 A1 | 3/2014 | Costello | |
| 2014/0163338 A1 | 6/2014 | Roesicke | |
| 2014/0206977 A1 | 7/2014 | Bahney et al. | |
| 2014/0257064 A1 | 9/2014 | Einck et al. | |
| 2014/0275862 A1 | 9/2014 | Kennedy | |
| 2014/0276220 A1 | 9/2014 | Briscoe et al. | |
| 2014/0343371 A1 | 11/2014 | Sowers, II et al. | |
| 2015/0057515 A1 | 2/2015 | Hagen et al. | |
| 2015/0112164 A1 | 4/2015 | Heikenfeld et al. | |
| 2015/0112165 A1 | 4/2015 | Heikenfeld | |
| 2016/0058354 A1 | 3/2016 | Phan et al. | |
| 2016/0066828 A1 | 3/2016 | Phan et al. | |
| 2016/0157768 A1 | 6/2016 | Braig et al. | |

FOREIGN PATENT DOCUMENTS

| | | |
|---|---|---|
| CN | 1969184 A | 5/2007 |
| CN | 1984716 A | 6/2007 |
| CN | 101380240 A | 3/2009 |
| CN | 101489470 A | 7/2009 |
| CN | 201508360 U | 6/2010 |
| EP | 0282349 A2 | 9/1988 |
| EP | 0453283 A1 | 10/1991 |
| EP | 0634215 A1 | 1/1995 |
| EP | 1500937 A1 | 1/2005 |
| EP | 1637889 A1 | 3/2006 |
| EP | 2551784 A1 | 1/2013 |
| JP | H07-77525 A | 3/1995 |
| JP | H08-504513 A | 5/1996 |
| JP | 2007503958 A | 3/2007 |
| JP | 2007532260 A | 11/2007 |

(56) References Cited

FOREIGN PATENT DOCUMENTS

| | | |
|---|---|---|
| JP | 2008505330 A | 2/2008 |
| JP | 200963597 A | 3/2009 |
| JP | 2009118420 A | 5/2009 |
| WO | 9011519 A1 | 10/1990 |
| WO | 9414062 A1 | 6/1994 |
| WO | 0014535 A1 | 3/2000 |
| WO | 01/88525 A1 | 11/2001 |
| WO | 2006133101 A2 | 12/2006 |
| WO | 2007097754 A1 | 8/2007 |
| WO | 2007146047 A1 | 12/2007 |
| WO | 2008083687 A1 | 7/2008 |
| WO | 2008095940 A1 | 8/2008 |
| WO | 2009004001 A1 | 1/2009 |
| WO | 2009019686 A2 | 2/2009 |
| WO | 2009052321 A2 | 4/2009 |
| WO | 2010017578 A1 | 2/2010 |
| WO | 2010045247 A1 | 4/2010 |
| WO | 2010075115 A2 | 7/2010 |
| WO | 2011117952 A1 | 9/2011 |
| WO | 2013152087 A2 | 10/2013 |
| WO | 2013181436 A1 | 12/2013 |
| WO | 2014001577 A1 | 1/2014 |
| WO | 2014025430 A2 | 2/2014 |
| WO | 2015120439 A1 | 8/2015 |
| WO | 2015184072 A1 | 12/2015 |
| WO | 2015184097 A2 | 12/2015 |
| WO | 2016049019 A1 | 3/2016 |
| WO | 2016061362 A2 | 4/2016 |
| WO | 2016090189 A1 | 6/2016 |
| WO | 2016130905 A1 | 8/2016 |
| WO | 2016138087 A1 | 9/2016 |
| WO | 2017019573 A1 | 2/2017 |
| WO | 2017019602 A1 | 2/2017 |
| WO | 2017070640 A1 | 4/2017 |

OTHER PUBLICATIONS

Sato, K. et al., "Pharmacologic responsiveness of isolated single eccrine sweat glands," American Journal of Physiology-Regulatory, Integrative and Comparative Physiology, vol. 240, No. 1, Jan. 1, 1981.
International Search Report and Written Opinion in International Patent Application No. PCT/US2017/047574, dated Nov. 16, 2017, 14 pgs.
International Searching Authority, Invitation to Pay Additional Fees and, Where Applicable, Protest Fee, and Communication Relating to the Results of the Partial International Search, issued in International Application No. PCT/US13/35092 dated Aug. 26, 2013, 9 pages.
International Searching Authority, Invitation to Pay Additional Search Fees and, Where Applicable, Protest Fee, and Communication Relating to the Results of the Partial International Search, issued in International Application No. PCT/US2014/061083 dated Dec. 15, 2014, 6 pages.
International Searching Authority, Invitation to Pay Additional Search Fees and, Where Applicable, Protest Fee, and Communication Relating to the Results of the Partial International Search, issued in International Application No. PCT/US2015/032843 dated Aug. 18, 2015, 2 pages.
International Searching Authority, Invitation to Pay Additional Search Fees and, Where Applicable, Protest Fee, and Communication Relating to the Results of the Partial International Search, issued in International Application No. PCT/US2015/032866 dated Aug. 31, 2015, 2 pages.
International Searching Authority, Invitation to Pay Additional Search Fees and, Where Applicable, Protest Fee, and Communication Relating to the Results of the Partial International Search, issued in International Application No. PCT/US2015/032893 dated Aug. 31, 2015, 2 pages.
International Searching Authority, Invitation to Pay Additional Search Fees and, Where Applicable, Protest Fee, and Communication Relating to the Results of the Partial International Search, issued in International Application No. PCT/US2015/040113 dated Dec. 1, 2015, 2 pages.
International Searching Authority, Search Report and Written Opinion in International Application No. PCT/US2016/043862, dated Oct. 19, 2016 (14 pages).
International Searching Authority, Search Report and Written Opinion issued in International Application No. PCT/US2014/061098 dated Dec. 12, 2014, 13 pages.
International Searching Authority, Search Report and Written Opinion issued in International Application No. PCT/US2016/018635 dated May 6, 2016, 12 pages.
International Searching Authority, Search Report and Written Opinion issued in International Application No. PCT/US2014/061083 dated Mar. 31, 2015, 18 pages.
International Searching Authority, Search Report and Written Opinion issued in International Application No. PCT/US2014/061098 dated Dec. 19, 2014, 13 pages.
International Searching Authority, Search Report and Written Opinion issued in International Application No. PCT/US2015/032830 dated Aug. 14, 2015, 9 pages.
International Searching Authority, Search Report and Written Opinion issued in International Application No. PCT/US2015/032843 dated Oct. 26, 2015, 11 pages.
International Searching Authority, Search Report and Written Opinion issued in International Application No. PCT/US2015/032866 dated Nov. 19, 2015, 12 pages.
International Searching Authority, Search Report and Written Opinion issued in International Application No. PCT/US2015/032893 dated Nov. 13, 2015, 14 pages.
International Searching Authority, Search Report and Written Opinion issued in International Application No. PCT/US2015/040113 dated Feb. 4, 2016, 13 pages.
International Searching Authority, Search Report and Written Opinion issued in International Application No. PCT/US2015/051439 dated Dec. 28, 2015, 7 pages.
International Searching Authority, Search Report and Written Opinion issued in International Application No. PCT/US2016/017726 dated May 12, 2016, 9 pages.
International Searching Authority, Search Report and Written Opinion issued in International Application No. PCT/US2016/050928 dated Nov. 29, 2016, 8 pages.
International Searching Authority, Search Report and Written Opinion issued in International Application No. PCT/US2016/059392 dated Feb. 15, 2017, 13 pages.
International Searching Authority, Search Report and Written Opinion issued in International Application No. PCT/US2017/013453 dated May 18, 2017, 14 pages.
International Searching Authority, Search Report and Written Opinion issued in International Application No. PCT/US2017/039421 dated Sep. 6, 2017, 10 pages.
International Searching Authority, Search Report and Written Opinion issued in International Application No. PCT/US2017/040588 dated Sep. 25, 2017, 11 pages.
International Searching Authority, Search Report and Written Opinion issued in International Application No. PCT/US2017/047574 dated Nov. 16, 2017, 14 pages.
International Searching Authority, Search Report and Written Opinion issued in International Application No. PCT/US2017/052651 dated Dec. 12, 2017, 14 pages.
International Searching Authority, Search Report and Written Opinion issued in International Application No. PCT/US2017/067495 dated Mar. 1, 2018, 10 pages.
Japanese Patent Office, Office Action issued in Japanese Application No. 2015-504702 dated Jan. 20, 2017, 7 pages (English language translation).
Kappelhoff, Bregt S., et al., "Pharmacokinetics of Nevirapine: Once-Daily Versus Twice-Daily Dosing in the 2NN Study," HIV Clinical Trials, Sep. 2005, vol. 6(5), pp. 254-261, Thomas Land Publishers, Inc. (9 pages).

(56) References Cited

OTHER PUBLICATIONS

Khurana, R.K. "Cholinergic dysfunction in Shy-Drager syndrome: Effect of the parasympathomimetic agent, bethanechol". Clinical Autonomic Research (1994) 4: 5. <https://doi.org/10.1007/BF01828832> (Year: 1994).

La Porte, C.J.L., et al., "Pharmacokinetics of Adjusted-Dose Lopinavir-Ritonavir Combined with Rifampin in Healthy Volunteers," Antimicrobial Agents and Chemotherapy, May 2004, vol. 48, No. 5, pp. 1553-1560, American Society for Microbiology (8 pages).

Lacy, Melinda K., et al., "Comparison of bactericidal activity after multidose administration of clarithromycin, azithromycin, and cefuroxime axetil aginst *Streptococcus pneumoniae*," International Journal of Antimicrobial Agents 10, 1998, pp. 279-283, Elsevier (5 pages).

Lai, Allen A., et al., "Time-course of interaction between carbamazepine and clonazepam in normal man," Clin. Pharmacol. Ther., Sep. 1978, vol. 24, pp. 316-323, The C.V. Mosby Co. (8 pages).

Lang, E., Spitzer, A., Claus, D., Neundorfer, B. and Handwerker, H. 0. Abstract of "Stimulation of sudomotor axon reflex mechanism by carbachol in healthy subjects and patients suffering from diabetic polyneuropathy". Acta Neurologica Scandinavica, 1995) 91: 251-254. (Year: 1995).

Marshall, William F., et al., "The Cephalosporins," Symposium on Antimicrobial Agents—Part V, Mayo Clin Proc, 1999, vol. 74, pp. 187-195 (9 pages).

McIlleron, Helen, et al., "Determinants of Rifampin, Isoniazid, Pyrazinamide, and Ethambutol Pharmacokinetics in a Cohort of Tuberculosis Patients," Antimicrobial Agents and Chemotherapy, Apr. 2006, vol. 50, No. 4, pp. 1170-1177, American Society for Microbiology (8 pages).

Medscape, "Drug, OTCs and Herbals | Medscape Reference," http://www.reference.medscapte.com/drugs, Accessed Mar. 2013 and Apr. 3, 2017 (1 page).

Mimaki, Takashi, "Clinical Pharmacology and Therapeutic Drug Monitoring of Zonisamide," Therapeutic Drug Monitoring, Dec. 1998, vol. 20(6), pp. 593-597, Lippincott Williams & Wilkins, Inc. (9 pages).

Mizuguchi, Hitoshi, et al., "A dual-electrode flow sensor fabricated using track-etched microporous membranes," Talanta, vol. 96, 2012, pp. 168-173, Elsevier (6 pages).

Mizuguchi, Hitoshi, et al., "A Triple-Electrode Based Dual-Biosensor System Utilizing Track-Etched Microporous Membrane Electrodes for the Silultaneous Determination of L-Lactate and D-Glucose," Bull. Chem. Co. Jpn., vol. 90, 2017, pp. 1211-1216, The Chemical Society of Japan (6 pages).

Molina, J-M., et al., "Pharmacokinetics of emtricitabine, didanosine andefavirenz administered once-daily for the treatment of HIV-infected adults (Pharmacokinetic substudy of the ANRS 091 trial)," HIV Medicine (2004), vol. 5, pp. 99-104, 2004 British HIV Association (6 pages).

Morse, Gene D., et al., "Multiple-Dose Pharmacokinetics of Delavirdine Mesylate and Didanosine in HIV-Infected Patients," Clin Drug Invest, 2003, pp. 323-328, vol. 23 (5), Adis Data Information BV (6 pages).

Munne P. International Programme on Chemical Safety Poisons Information Monograph 181, "Pharmacology and Toxicology," Published Apr. 1990, available at: http://www.inchem.org/documents/pims/pharm/pim181.htm#PartTitle:7.%20%20PHARMACOLOGY%20AND%20TOXICOLOGY, Accessed Oct. 2, 2009, pp. 14-18 (5 pages).

Nauta, Ernst H., et al., "Dicloxacillin and cloxacillin: Pharmacokinetics in healthy and hemodialysis subjects," Clinical Pharmacology and Therapeutics, vol. 20, No. 1, Feb. 13, 1976, pp. 98-108 (11 pages).

Ochs, Hermann R., et al., "Digitoxin Accumulation," Br. J. clin. Pharmac. (1982), vol. 14, pp. 225-229. The Macmillan Press Ltd 1982 (5 pages).

Office Action in U.S. Appl. No. 15/314,410, dated Feb. 27, 2020, 7 pgs.

Office Action in U.S. Appl. No. 15/314,410, dated Jul. 9, 2019, 6 pgs.

Office Action in U.S. Appl. No. 15/551,306, dated Dec. 20, 2019, 12 pgs.

Supplementary Search Report in European Patent Application No. 17821438.3, 7 pgs.

Agwuh, Kenneth N., et al., "Pharmacokinetics and pharmacodynamics of the tetracyclines including glycylcyclines," Journal of Antimicrobial Chemotherapy, 2006, vol. 58, pp. 256-265, Advance Access Publication (10 pages).

Argatroban Injection, Package Insert for Argatroban Injection, "Highlights of Prescribing Information," Research Triangle Park, NC, GlaxoSmithKline, 2012 (22 pages).

Australian Patent Office, Notice of Acceptance for Patent Application issued in Australian Application No. 2013243541 dated Mar. 23, 2017 (3 pages).

Australian Patent Office, Patent Examination Report No. 1 issued in Australian Application No. 2013243541 dated Nov. 25, 2016, 4 pages.

Balant-Gorgia, Androniki E., et al., "Clinical Pharmacokinetics of Clompipramine," Clin. Pharmacokinet., vol. 20(6), 1991, pp. 447-462 (16 pages).

Basi, Thin-layer Cell Gaskets, https://www.basinc.com/products/ec/gaskets[Oct. 10, 2017 2:43:33 PM] (8 pages).

Baxter, Roger, et al., "Comparison of Bactericidal Activity of Five Antibiotics against *Staphylococcus aureus*," Oxford Journals, The Journal of Infectious Diseases, vol. 161, No. 5, May 1990, pp. 1023-1025, Oxford University Press (4 pages).

Bertrand, Julie, et al., "Influence of pharmacogenetics on indinavir disposition and short-term response in HIV patients initiating HAART," Eur J Clin Pharmacol., Jul. 22, 2010, vol. 65(7), pp. 667-678 (17 pages).

Bockbrader, Howard N., et al., "Clinical Pharmacokinetics of Pregabalin in Healthy Volunteers," Journal of Clinical Pharmacology, 2010, vol. 50, pp. 941-950 (10 pages).

Buch, A.B., et al., "A Study of Pharmacokinetic Interaction Between Buspirone and Alprazolam at Steady State," J Clin Pharmacol, 1993, vol. 33, pp. 1104-1109 (6 pages).

Chinese Office Action in Chinese Patent Application No. 201580039933.4 (English language translation), dated Mar. 5, 2020, 9 pgs.

Chinese Patent Office, English translation of Office Action issued in corresponding Chinese Application No. 201480067960.8, dated Dec. 11, 2018, 3 pages.

Chinese Patent Office, First Office Action issued in Chinese Application No. 201380028053.8 dated Dec. 21, 2015, 4 pages.

Chinese Patent Office, Second Office Action issued in Chinese Application No. 201380028053.8 dated Sep. 20, 2016, 8 pages (including English language translation).

Chinese Patent Office, Third Office Action issued in Chinese Application No. 201380028053.8 dated Mar. 20, 2017, 17 pages (including English language translation).

De Jong, J. et al., "Membranes and microfluidics: a review," Lab Chip, 2006, 6, 1125-1139 (15 pages).

Dhote, V., Bhatnagar, P., Mishra, P. K., Mahajan, S. C., & Mishra, D. K. (2012). Iontophoresis: a potential emergence of a transdermal drug delivery system;Scientia pharmaceutica 80(1), 1-28. doi:10.3797/sciphamn.1108-20 (Year: 2012).

European Official Letter in European Patent Application No. 16831190.0, dated Jan. 31, 2020, 5 pgs.

European Patent Office, Extended European Search Report issued in European Application No. 15800539.7, dated Aug. 17, 2018 (6 pages).

European Patent Office, Extended European Search Report issued in European Application No. 15819306.0-1115 dated Feb. 9, 2018 (9 pages).

European Patent Office, Extended European Search Report issued in European Application No. 16753129.2, dated Jun. 15, 2018 (8 pages).

European Patent Office, extended European Search Report issued in European Patent Application No. 16831190.0, dated Jan. 30, 2019 (8 pages).

(56) References Cited

OTHER PUBLICATIONS

European Patent Office, Extended Search Report issued for European Application No. 15800043.0-1115 dated Apr. 16, 2018, 11 pages.
European Patent Office, Extended Search Report issued in European Application No. 15844313.5 dated Mar. 15, 2018, 15 pages.
European Patent Office, Official Communication for EP Application No. 13 718 933.8-1101 dated Feb. 14, 2018 (5 pages).
European Patent Office, Partial European Search Report issued in European Application No. 15800043.0-115 dated Jan. 8, 2018, 13 pages.
European Patent Office, Partial European Search Report issued in European Application No. 16203346.8-1657 dated Mar. 24, 2017, 7 pages.
European Patent Office, Supplemental European Search Report issued in European Application No. 15799317.1-1657 dated Dec. 21, 2017, 9 pages.
European Patent Office, Supplemental European Search Report issued in European Application No. 15799514.3-1657 dated Dec. 7, 2017, 8 pages.
European Patent Office, Supplementary European Search Report issued in European Application No. EP 16749949, dated Jun. 15, 2018 (7 pages).
European Patent Office, Written Opinion of the International Search Authority / International Preliminary Report on Patentability for PCT/US2013/035092 dated Oct. 16, 2014 (14 pages).
European Search Opinion in European Patent Application No. 16860910.5, dated Jun. 27, 2019, 4 pgs.
European Search Report in European Patent Application No. 19173145.4, 6 pgs.
European Search Report in European Patent Application No. 19173149.6, 6 pgs.
European Search Report in European Patent Application No. 19188927.8, dated Oct. 23, 2019, 9 pgs.
European Supplementary Search Report in European Patent Application 16845111, dated Mar. 14, 2019, 9 pgs.
European Supplementary Search Report in European Patent Application No. 16860910.5, 4 pgs.
Fonseca, Walter, et al., "Comparing Pharmacokinetics of Amoxicillin Given Twice or Three Times per Day to Children Older than 3 Months with Pneumonia," Antimicrobial Agents and Chemotherapy, Mar. 2003, vol. 47, No. 3, pp. 997-1001, American Society for Microbiology (5 pages).
Friedrich, Lawrance V., et al., "Aztreonam Pharmacokinetics in Burn Patients," Antimicrobial Agents and Chemotherapy, Jan. 1991, vol. 35, No. 1, pp. 57-61, American Society for Microbiology (5 pages).
Fu et al., "Controlled Reagent Transport in Disposable 2D Paper Networks", The Royal Society of Chemistry 2010, Lab Chip, 2010, 10, 918-920.
Garcia, David A., et al., "Parenteral Anticoagulants: Antithrombotic Therapy and Prevention of Thrombosis, 9th ed: American College of Chest Physicians Evidence-Based Clinical Practice Guidelines," Chest, 2012, vol. 141/2 (Supplement), pp. e24S-e43S (20 pages).
Geller, David E., et al., :Pharmacokinetics and Bioavailability of Aerosolized Tobramycin in Cystic Fibrosis, Chest, vol. 122, No. 1, Jul. 2002, pp. 219-226 (8 pages).
Gibbons et al., QDIRT: Quantitative Direct and Indirect Testing of Sudomotor Function, Jun. 2008 (Year: 2008).
Gibbons et al., Sweat Testing to evaluate autonomic function, Apr. 2009, NIH (Year: 2009).
Glazer, William M., et al., "The determination of the steady-state pharmacokinetic profile of fluphenazine decanoate by gas chromatography/mass spectrometry detection," Schizophrenia Research, 1992, vol. 8, pp. 111-117, Elsevier Science Publishers B.V. (7 pages).
Goodwin, Megan L., et al., "Antifungal serum concentration monitoring: an update," Journal of Antimicrobial Chemotherapy, 2008, vol. 61, pp. 17-25, Advance Access publicaiton Nov. 12, 2007 (9 pages).

Hsu, Ann, et al., "Multiple-Dose Pharmacokinetics of Ritonavir in Human Immunodeficiency Virus-Infected Subjects," Antimicrobial Agents and Chemotherapy, May 1997, Vo. 41, No. 5, pp. 898-905, American Society for Microbiology (8 pages).
Hyland, R., et al., "Identification of the Cytochrome P450 Enzymes Involved in the N-Oxidation of Voriconazole," Drug Metabolism and Disposition, Jan. 2003, vol. 31, No. 5, pp. 540-547, The American Society for Pharmacology and Experimental Therapeutics (8 pages).
Illigens et al., Sweat testing to evaluate autonomic function, Nov. 2008 (Year: 2008).
International Bureau, Notification Concerning Transmittal of International Preliminary Report on Patentability issued in International Application No. PCT/US2013/035092 dated Oct. 16, 2014, 14 pages.
Office Action in U.S. Appl. No. 15/680,611, dated Jan. 29, 2020, 21 pgs.
Office Action in U.S. Appl. No. 15/680,611, dated Jul. 25, 2019, 25 pgs.
Office Action in U.S. Appl. No. 15/757,465, dated Apr. 20, 2020, 15 pgs.
Ordonez Gallego, A., et al., "Oxycodone: a pharmacological and clinical review," Clin Transl Oncol, 2007, vol. 9, pp. 298-307 (10 pages).
Paixao, Thiago Regis Longo Cesar, et al., "The use of a new twin-electrode thin-layer cell to the study of homogeneous processes coupled to electrode reactions," Journal of Electroanalytical Chemistry, vol. 596, 2006, pp. 101-108, Elsevier (8 pages).
Pike, Douglas J., et al., "Flow Cell Design for Effective Biosensing," Sensors, ISSN 1424-8220, Dec. 2012, vol. 13, pp. 58-70, www.mdpi.com/journal/sensors, 13 pages.
Pippenger, C.E., et al., "Principles of Therapeutic Drug Monitoring," In: Wong SHY, ed. Therapeutic Drug Monitoring and Toxicology by Liquid Chromatography. Boca Raton, FL: CRC Press, 1985, pp. 11-36 (26 pages).
Preston, ScienceDirect (Year: 2013).
Purkins, L., et al., "Pharmacokinetics and Safety of Voriconazole following Intravenous-to Oral-Dose Escalation Regimens," Antimicrobial Agents and Chemotherapy, Aug. 2002, vol. 46, No. 8, pp. 2546-2553, American Society for Microbiology (8 pages).
Purkins, Lynn, et al., "The pharmacokinetics and safety of intravenous voriconazole—a novel wide-spectrum antifungal agent," Br J Clin Pharmacol, 2003, vol. 56, pp. 2-9, Blackwell Publishing Ltd (8 pages).
Ratjen, F., et al., "Pharmacokinetics of inhaled colistin in patients with cystic fibrosis," Journal of Antimicrobial Chemotherapy, 2006, vol. 57, pp. 306-311 (6 pages).
Remmel, Rory P., et al., "Simultaneous Assay of Felbamate plus Carbamazepine, Phenytoin, and Their Metabolites by Liquid Chromatography with Mobile Phase Optimization," Therapeutic Drug Monitoring, 1990, vol. 12, pp. 90-96, Raven Press, Ltd., New York (7 pages).
Rosenfeld, W.E., et al., "Comparison of the Steady-State Pharmacokinetics of Topiramate and Valproate in Patients with Epilepsy During Monotherapy and Concomitant Therapy," Epilepsia, 1997, vol. 38(3), pp. 324-333, Lippincott-Raven Publishers, Philadelphia (10 pages).
Ruslami, Rovina, et al., "Pharmacokinetics and Tolerability of a Higher Rifampin Dose versus the Standard Dose in Pulmonary Tuberculosis Patients," Antimicrobial Agents and Chemotherapy, Jul. 2007, vol. 51, No. 7, pp. 2546-2551, American Society for Microbiology (6 pages).
Rythmol, Package Insert for Rythmol, "Highlights of Prescribing Information," Reliant Pharmaceuticals Inc., 2004 (24 pages).
Sadler, Brian M., et al., "Pharmacokinetic and Pharmacodynamic Study of the Human Immunodeficiency Virus Protease Inhibitor Amprenavir after Multiple Oral Dosing," Antimicrobial Agents and Chemotherapy, Jan. 2001, vol. 45, No. 1, pp. 30-37, American Society for Microbiology (8 pages).
Shibasaki M, Crandall CG. "Effect of local acetylcholinesterase inhibition on sweat rate in humans". J Appl Physiol. (2001) 90(3): 757-762 (Year: 2001).

(56) References Cited

OTHER PUBLICATIONS

Silverstein, Jeffrey H., et al., "An Analysis of the Duration of Fentanyl and Its Metabolites in Urine and Saliva," Anesth Analg, 1993, vol. 76:6, pp. 618-621, The International Anesthesia Research Society (4 pages).

Sobue, Satoshi, et al., "Pharmacokinetics of fosfluconzaole and fluconazole following multiple intravenous administration of fosfluconazole in healthy male volunteers," British Journal of Clinical Pharmacology, 2004, vol. 58:1, pp. 20-25, Blackwell Publishing Ltd. (6 pages).

Song et al., Aptamer-based biosensors, Trac Trends in Analytical Chemistry, vol. 27, No. 2, Dec. 23, 2007, pp. 108-117.

Sonner, Z., et al., "The microfluidics of the eccrine sweat gland, including biomarker partitioning, transport, and biosensing implications," Biomicrofluidics, vol. 9, pp. 031301-1-031301-19, CrossMark, 19 pages, 2015.

Spencer, H.J. "Programmable nanoampere constant current sources for iontophoresis". Med. & biol. Engng. (1971) 9:693. https://doi.org/10.1007/BF02474650 <https://doi.org/10.1007/BF02474650> (Year: 1971).

Stoppa, Matteo, et al., "Wearable Electronics and Smart Tectiles: A Critical Review," Sensors, 2014, pp. 11957-11992, vol. 14 (36 pages).

Ti, Teow-Yee, et al., "Disposition of Intravenous Metronidazole in Asian Surgical Patients," Antimicrobial Agents and Chemotherapy, Oct. 1996, vol. 40, No. 10, pp. 2248-2251, American Society for Microbiology (4 pages).

Viracept, Package Insert for Viracept, "Highlights of Prescribing Information," Agouron Pharmaceuticals, 2008 (27 pages).

Von Hentig, Nils, et al., "Pharmacokinetics of Saquinavir, Atazanavir, and Ritonavir in a Twice-Daily Boosted Double-Protease Inhibitor Regimen," Antimicrobial Agents and Chemotherapy, Apr. 2007, vol. 51, No. 4, pp. 1431-1439, American Society for Microbiology (9 pages).

Wilens, Timothy E., et al., "Fluoxetine Pharmacokinetics in Pediatric Patients," Journal of Clinical Psychopharmacology, 2002, vol. 22, No. 6, pp. 568-575, Lippincott Williams & Wilkins, Inc. (8 pages).

Wong, Steven H.Y., "Therapeutic Drug Monitoring and Toxicology by Liquid Chromatography," Chromatographic Science Series, 1985, vol. 32, Chapter 2 "Principles of Therapeutic Drug Monitoring" by C.E. Pippenger, Marcel Dekker, Inc., New York and Basel (34 pages).

Yamamoto, Takatsugu, et al., "Pharmacokinetic Characteristics of Minocycline in Debilitated Elderly Patients," American Journal of Therapeutics, 1999, vol. 6, pp. 157-160 (4 pages).

Yamazaki, T. et al., "Smart Integrated Sensor for Multiple Detections of Glucose and L-Lactate Using On-Chip Electrochemical System," Journal of Sensors, vol. 2011, Article ID 190284, doi:10.1155/2011/190284, Accepted Apr. 26, 2011, 7 pages.

Zyprexa Relprew, Package Insert for Zyprexa Relprevv, "Highlights of Prescribing Information," Eli Lilly and Company, 2008 (27 pages).

DEVICES WITH REDUCED MICROFLUIDIC VOLUME BETWEEN SENSORS AND SWEAT GLANDS

CROSS-REFERENCE TO RELATED APPLICATIONS

This application is a national stage application under 35 U.S.C. § 371 of International Application No. PCT/US2017/040588, filed on Jul. 3, 2017, which claims priority to U.S. Provisional Application No. 62/357,643 filed Jul. 1, 2016, the disclosures of which are hereby incorporated by reference herein in their entireties.

BACKGROUND

Sweat sensing technologies have enormous potential for applications ranging from athletics, to neonatology, to pharmacological monitoring, to personal digital health, to name a few applications. Sweat contains many of the same biomarkers, chemicals, or solutes that are carried in blood and can provide significant information enabling one to diagnose illness, health status, exposure to toxins, performance, and other physiological attributes even in advance of any physical sign. Furthermore, sweat itself, the action of sweating, and other parameters, attributes, solutes, or features on, near, or beneath the skin can be measured to further reveal physiological information.

If sweat has such significant potential as a sensing paradigm, then why has it not emerged beyond decades-old usage in infant chloride assays for Cystic Fibrosis or in illicit drug monitoring patches? In decades of sweat sensing literature, the majority of medical literature utilizes the crude, slow, and inconvenient process of sweat stimulation, collection of a sample, transport of the sample to a lab, and then analysis of the sample by a bench-top machine and a trained expert. This process is so labor intensive, complicated, and costly that in most cases, one would just as well implement a blood draw since it is the gold standard for most forms of high performance biomarker sensing. Hence, sweat sensing has not emerged into its fullest opportunity and capability for biosensing, especially for continuous or repeated biosensing or monitoring. Furthermore, attempts at using sweat to sense "holy grails" such as glucose have not yet succeeded to produce viable commercial products, reducing the publically perceived capability and opportunity space for sweat sensing.

Of all the other physiological fluids used for bio monitoring (e.g. blood, urine, saliva, tears), sweat has arguably the least predictable sampling rate in the absence of technology. However, with proper application of technology, sweat can be made to outperform other non-invasive or less invasive biofluids in predictable sampling. For example, it is difficult to control saliva or tear rate without negative consequences for the user (e.g., dry eyes, tears, dry mouth, or excessive saliva while talking). Urine is also a difficult fluid for physiological monitoring, because it is inconvenient to take multiple urine samples, it is not always possible to take a urine sample when needed, and control of biomarker dilution in urine imposes further significant inconveniences on the user or test subject.

However, the state of art in sweat bio monitoring is in need of additional devices and methods to properly reduce the volume between sensors and skin. Reducing sweat volume is critical for fast sampling times or for sampling during intervals with very low sweat rates. In addition, it also may be critical for prolonged stimulation (i.e., where less stimulation is required), and for improving biomarker measurements where a low sweat rate is required to ensure correlation between biomarker concentrations in sweat and those in blood.

Biosensing using sweat has many drawbacks and limitations that must be resolved in a manner that affordably, effectively, conveniently, intelligently, and reliably brings sweat sensing technology into intimate proximity with sweat as it is generated.

SUMMARY OF THE INVENTION

Embodiments of the disclosed invention provide a sweat sensing device capable of reduced volume between the sensors and sweat glands, which decreases the sampling interval. In one embodiment, a sweat sensing device for sensing sweat on the skin includes one or more sweat sensors, a sweat collector placed on or adjacent to the skin with one or more pores or pathways for entry of sweat from the skin into the sweat collector, the sweat collector at least partly defining a sweat volume between the analyte-specific sensor and the skin, and a pressure element capable of holding the sweat collector against the skin with a pressure and reducing the sweat volume between the sweat collector and the skin.

The objects and advantages of the disclosed invention will be further appreciated in light of the following detailed descriptions and drawings.

DEFINITIONS

As used herein, "chronological assurance" is an assurance of the sampling rate for measurement(s) of sweat, or solutes in sweat, being the rate at which measurements can be made of new sweat or its new solutes as they originate from the body. Chronological assurance may also include a determination of the effect of sensor function, or potential contamination with previously generated sweat, previously generated solutes, other fluid, or other measurement contamination sources for the measurement(s).

As used herein, "sweat sampling rate" is the effective rate at which new sweat, or sweat solutes, originating from the sweat gland or from skin or tissue, reaches a sensor that measures a property of sweat or its solutes. Sweat sampling rate, in some cases, can be far more complex than just sweat generation rate. Sweat sampling rate directly determines, or is a contributing factor in determining the chronological assurance. Times and rates are inversely proportional (rates having at least partial units of l/seconds), therefore a short or small time required to refill a sweat volume can also be said to have a fast or high sweat sampling rate. The inverse of sweat sampling rate (l/s) could also be interpreted as a "sweat sampling interval(s)". Sweat sampling rates or intervals are not necessarily regular, discrete, periodic, discontinuous, or subject to other limitations. Like chronological assurance, sweat sampling rate may also include a determination of the effect of potential contamination with previously generated sweat, previously generated solutes, other fluid, or other measurement contamination sources for the measurement(s). Sweat sampling rate can also be in whole or in part determined from solute generation, transport, advective transport of fluid, diffusion transport of solutes, or other factors that will impact the rate at which new sweat or sweat solutes reach a sensor and/or are altered by older sweat or solutes or other contamination sources. Sensor response times may also affect sampling rate.

As used herein, "sweat generation rate" is the rate at which sweat is generated by the sweat glands themselves. Sweat generation rate is typically measured by the flow rate from each gland in nL/min/gland. In some cases, the measurement is then multiplied by the number of sweat glands from which the sweat is being sampled.

As used herein, "measured" can imply an exact or precise quantitative measurement and can include broader meanings such as, for example, measuring a relative amount of change of something. Measured can also imply a binary measurement, such as 'yes' or 'no' type measurements.

As used herein, "sweat volume" refers to a fluidic volume. Sweat volume may be the volume that exists between a sensor and the point of generation of sweat or a solute moving into or out of sweat from the body or from other sources. Sweat volume can include the volume that can be occupied by sweat between: the sampling site on the skin and a sensor on the skin where the sensor has no intervening layers, materials, or components between it and the skin; or the sampling site on the skin and a sensor on the skin where there are one or more layers, materials, or components between the sensor and the sampling site on the skin. Sweat volume may refer to the sweat volume of multiple integrated components, or used in description of the sweat volume for single component or a subcomponent, or in the space between a component or a device and skin.

As used herein, a "volume-reducing component" is any component, material, element, feature, or combinations thereof that enables formation of a volume-reduced pathway and that transports sweat to at least one sensor specific to at least one analyte in sweat.

As used herein, a "volume-reduced pathway" is a sweat volume that has been reduced at least in part by addition a volume-reducing component, which therefore decreases the sweat sampling interval for a given sweat generation rate.

As used herein, "microfluidic components" are channels in polymer, textiles, paper, or other components known in the art for guiding movement of a fluid or at least partial containment of a fluid.

As used herein, "sweat collector" is a component that at least in part is pressed directly against the skin, and which is at least a part of a volume-reducing component. Specifically, a sweat collector includes one or more, or a plurality, of pores or pathways in a material and/or on the surface of a material that is held against skin so that the plasticity of skin allows skin defects, hair, and other sweat volume increasing aspects of skin to at least partially conform against the material.

As used herein, "space between the sweat collector and skin" refers to the space between the skin and a sweat collector that would be filled by air, skin oil, or other non-sweat fluids or gases if no sweat existed. This space could be filled by sweat by positive pressure generated by the sweat glands, or for example by wicking, or by other suitable methods.

As used herein, "pressure element" is any component that at least in part provides pressure to a sweat collector to create at least in part a reduced sweat volume between a sweat collector and skin.

As used herein, the term "analyte-specific sensor" is a sensor specific to an analyte and performs specific chemical recognition of the presence or concentration of the analyte (e.g., ion-selective electrodes, enzymatic sensors, electrochemical aptamer-based sensors, etc.). For example, sensors that sense impedance or conductance of a fluid, such as biofluid, are excluded from the definition of "analyte-specific sensor" because sensing impedance or conductance merges measurements of all ions in biofluid (i.e., the sensor is not chemically selective; it provides an indirect measurement). An exemplary analyte-specific sensor is an ion-selective electrode for potassium. A sensor for cortisol, which only has interference (non-specificity) to estrogen, would still be specific to one analyte because there are many instances in which estrogen would not be changing, cortisol would be changing, and the sensor would effectively be specific to cortisol. Sensors could also be optical, mechanical, or use other physical/chemical methods which are specific to a single analyte. Further, multiple sensors can each be specific to one of multiple analytes.

DETAILED DESCRIPTION OF THE INVENTION

To understand the proper numerical values or representations of sweat sampling rate and therefore chronological assurance, sweat generation rate and sweat volumes should be understood. From 'Dermatology: an illustrated color text" 5th edition, the maximum sweat generated per person per day is 10 liters which on average is 4 µL per gland maximum per day, or about 3 nL/min/gland. This is about 20× higher than the minimum sweat generation rate. The maximum stimulated sweat generation rate according to Buono 1992, J. Derm. Sci. 4, 33-37, "Cholinergic sensitivity of the eccrine sweat gland in trained and untrained men", the maximum sweat generation rate by pilocarpine stimulation are about 4 nL/min/gland for untrained men and 8 nL/min/gland for trained (exercising often) men. Other sources indicate maximum sweat generation rates of an adult can be up to 2-4 liters per hour or 10-14 liters per day (10-15 g/min·m$^2$), which based on the per hour number translates to 20 nL/min/gland or 3 nL/min/gland. Sweat stimulation data from "Pharmacologic responsiveness of isolated single eccrine sweat glands" by K. Sato and F. Sato (the data was for extracted and isolated monkey sweat glands, which are very similar to human ones) suggests a sweat generation rate up to about 5 nL/min/gland is possible with stimulation, and several types of sweat stimulating substances are disclosed. For simplicity, we can assume for use in calculations in the disclosed invention (but not so limit the disclosed invention) that the minimum sweat generation rate on average is about 0.1 nL/min/gland and the maximum sweat generation rate is about 5 nL/min/gland, which is about a 50× difference between the two.

Based on the assumption of a sweat gland density of 100/cm$^2$, a sensor that is 0.55 cm in radius (1.1 cm in diameter) would cover about 1 cm$^2$ area or approximately 100 sweat glands. Next, assume a sweat volume under a skin-facing sensor (space between the sensor and the skin) of 100 μm average height or 100E-4 cm, and that same 1 cm$^2$ area, which provides a sweat volume of 100E-4 cm$^3$ or about 100E-4 mL or 10 μL of volume. With the maximum sweat generation rate of 5 nL/min/gland and 100 glands, it would require a 20 minutes to fully refresh the sweat volume (using first principles/simplest calculation only). With the minimum sweat generation rate of 0.1 nL/min/gland and 100 glands, it would require 1000 minutes or about 17 hours to refresh the sweat volume. Because the flow is not entirely centered, according to Sonner, et al., in Biomicrofluidics, 2015 May 15; 9(3):031301, doi: 10.1063/1.4921039, the time to fully refresh the sweat sample (e.g. new sweat replaces all old sweat) could be 6× longer or more. For slow flow rates of sweat, back-diffusion of analytes and other confounding factors could make the effective sampling interval even worse. Clearly, conventional approaches with large sweat volumes and slow sampling intervals can be problematic for continuous monitoring of sweat samples.

Sweat stimulation, or sweat activation, can be achieved by known methods. For example, sweat stimulation can be achieved by simple thermal stimulation, chemical heating pad, infrared light, by orally administering a drug, by intradermal injection of drugs such as carbachol, methylcholine, or pilocarpine, and by dermal introduction of such drugs using iontophoresis, but sudo-motor-axon reflex sweating, or by other means. A device for iontophoresis may, for example, provide direct current and use large lead electrodes lined with porous material, where the positive pole is dampened with 2% pilocarpine hydrochloride and the negative one with 0.9% NaCl solution. Sweat can also be controlled or created by asking the subject using the patch to enact or increase activities or conditions that cause them to sweat.

Aspects of the disclosed invention apply at least to any type of sweat sensing device that stimulates sweat, measures sweat, sweat generation rate, sweat chronological assurance, its solutes, solutes that transfer into sweat from skin, a property of or things on the surface of skin, or properties or things beneath the skin. Any suitable sensor may be used in the disclosed invention (e.g. ion-selective, enzymatic, antibody, aptamer, optical, electrical, mechanical, etc.). Further, aspects of the disclosed invention apply to sweat sensing devices that can take on forms including patches, bands, straps, portions of clothing, wearables, or any suitable mechanism that reliably brings sweat stimulating, sweat collecting, and/or sweat sensing technology into intimate proximity with sweat as it is generated. Some embodiments of the disclosed invention utilize adhesives to hold the device near the skin, but devices could also be held by other mechanisms that hold the device secure against the skin, such as a strap or embedding in a helmet.

Certain embodiments of the disclosed invention show sensors as individual elements. It is understood that many sensors require two or more electrodes, reference electrodes, or additional supporting technology or features that are not captured in the description herein. Sensors are preferably electrical in nature, but may also include optical, chemical, mechanical, or other known biosensing mechanisms. Sensors can be in duplicate, triplicate, or more, to provide improved data and readings. Sensors may be referred to by what the sensor is sensing, for example: a sweat sensor; an impedance sensor; a sweat volume sensor; a sweat generation rate sensor; and a solute generation rate sensor. Certain embodiments of the disclosed invention show sub-components of what would be sweat sensing devices with more sub-components that would be used in the device in various applications (e.g., a battery) and, for purpose of brevity and focus on inventive aspects, are not explicitly shown in the diagrams or described in the embodiments of the disclosed invention. As a further example, many embodiments of the disclosed invention could benefit from mechanical or other techniques known to those skilled in wearable devices, patches, bandages, and other technologies or materials affixed to skin, to keep the devices or sub-components of the skin firmly affixed to skin or with pressure favoring constant contact with skin or conformal contact with even ridges or grooves in skin, and are included within the spirit of the disclosed invention. The present application has specification that builds upon International Patent Application No. PCT/US2013/035092, the disclosure of which is hereby incorporated herein by reference in its entirety.

Embodiments of the disclosed invention include at least one analyte-specific sensor, a sweat collector, and at least one component that presses the sweat collector against skin in order to create a volume reduced pathway. The sweat collector includes a plurality of pores or porous pathways to allow sweat to enter into the sweat collector from a plurality of sweat ducts beneath the sweat collector.

Figure 1A:
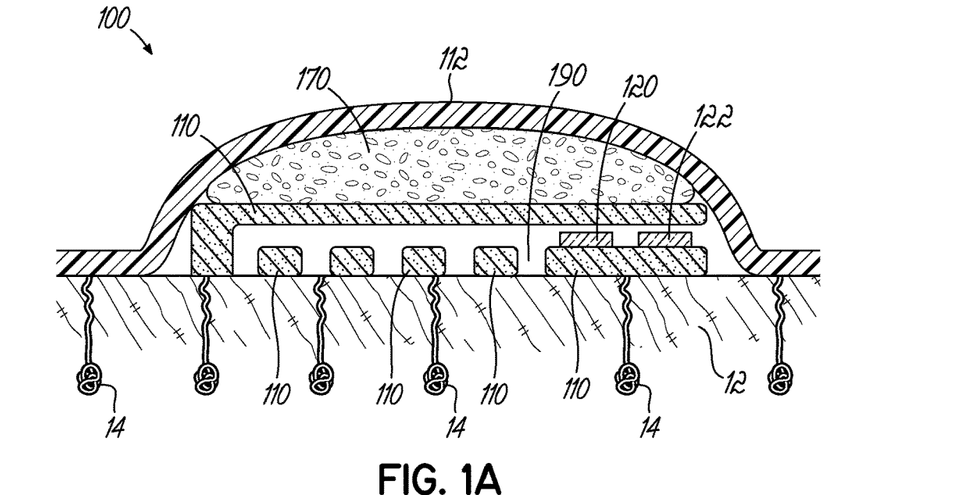
FIG. 1A is a cross-sectional view of a portion of a device for sweat biosensing with a reduced microfluidic volume according to an embodiment of the disclosed invention.
Figure 1B:
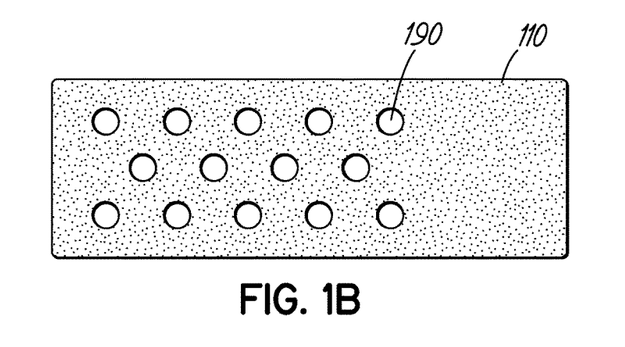
FIG. 1B is a top cross-sectional view of the sweat collector of the device of FIG. 1A.

With reference to FIGS. 1A and 1B, in an embodiment, a sweat sensing device 100 is placed on or near skin 12 creating a reduced sweat volume. For the figures and description, like numerals refer to like features featured in other embodiments and figures. The device 100 includes a medical textile 112 with adhesive that presses a sweat collector 110 against the skin 12. The sweat collector 110 comprises a plurality of pores and an open channel that form a sweat volume 190 through which sweat is transported to the sensors 120, 122, at least one of which is an analyte-specific sensor. In an embodiment, the sensors 120, 122 are positioned on an interior surface of the sweat collector 110. The pores may range from nm's to mm's in diameter and in length for example. The sweat collector 110 may have dimensions that support a sweat volume capacity of nL's to μL's. The pores of the sweat collector 110 are shown in FIG. 1B. The sweat collector 110 may be, for example, a molded polymer such as acrylic. The open channel in the sweat collector 110 may include supports, such as spacer beads or posts (not shown). To provide even and steady application of pressure, the device 100 also includes a memory foam 170. Even if the skin had defects, hairs, roughness, etc., enough pressure is applied such that positive pressure of sweat generated by sweat glands causes sweat to preferentially permeate through the pores in the sweat collector 110 and not between the sweat collector 110 and the skin 12 or around the device 100. This same applied pressure also therefore minimizes the sweat volume between the sweat collector 110 and the skin 12.

With further reference to FIG. 1A, the applied pressure must be great enough to provide a reduced sweat volume between the sweat collector 110 and the skin 12 but not so great as to prevent sweat from flowing into the sweat collector 110. Although skin deformation varies from person to person and based on measurement location and skin hydration level as well, generally, a pressure of 5,000-30,000 N/m$^2$ should yield a mechanical deformation between 0.6 to 1.6 mm of skin deformation under direct compression. In an embodiment of the disclosed invention, generally about 100 μm of indentation/deformation may be provided by the device 100. An experimentally measured value of about 100 μm can be achieved within 15 minutes of pressure ranging from 60 to 40,000 N/m$^2$, from 60 to 4,000 N/m$^2$, from 60 to 600 N/m$^2$, from 600 to 4,000 N/m$^2$, or from 600 to 40,000 N/m$^2$. In embodiments of the disclosed invention, a device may be applied with a pressure range for the sweat collector 110 against skin of at least 60 N/m$^2$, at least 600 N/m$^2$, at least 4,000 N/m$^2$, or at least 40,000 N/m$^2$. The maximum pressure that could occlude a highly active sweat gland is 70,000 N/m$^2$ for 15 nL/min/gland as calculated by Sonner et al. in Biomicrofluidics. 2015 May 15; 9(3): 031301. doi: 10.1063/1.4921039. Therefore, at lower sweat rates, lower applied pressures may be utilized because the hydraulic pressure created by the sweat glands is lower than at higher sweat rates. The applied pressure should be designed to avoid any issue with long-term pressure against the skin that creates skin damage or issues with blood flow. Further, embodiments of the disclosed invention may include a plurality of pressure providing components that are used in combination with each other. Suitable pressure providing components include a strap, a plastic housing, a clamp, a compressible component (e.g., memory foam), a spring, vacuum, or a combination thereof (e.g. a strap and a vacuum; a plastic housing and a vacuum; or a clamp, a memory foam component, and a strap, etc.).

Figure 2:
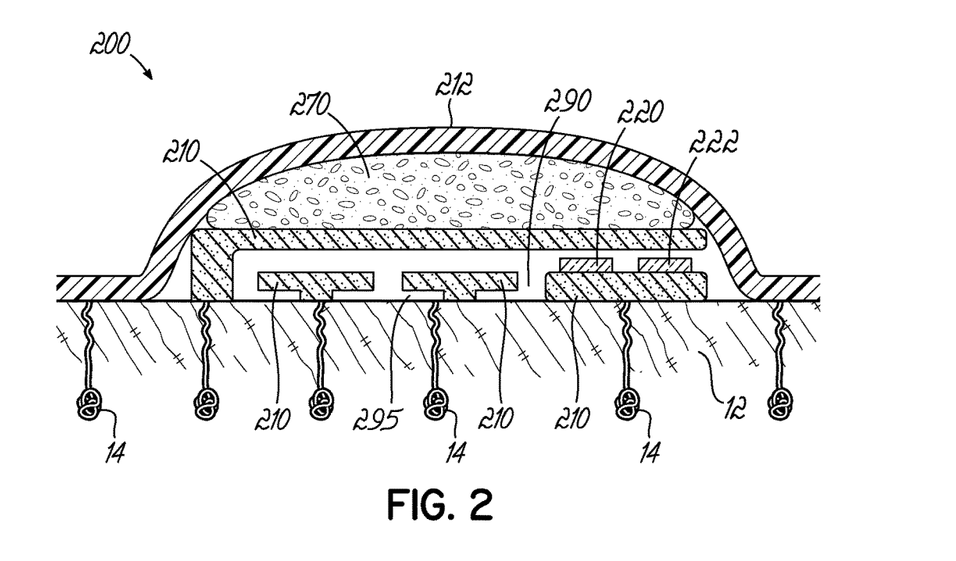
FIG. 2 is a cross-sectional view of a portion of a device for sweat biosensing with a reduced microfluidic volume according to another embodiment.

With reference to FIG. 2, in an embodiment of the disclosed invention, a device 200 is shown. The device 200 is similar to the device 100 with a variation being that pathways 295 are included to increase the open area 290 of the sweat collector 210 pressed against the skin 12. Numerous methods could be used to achieve such pathways, including use of porous membranes, textiles, open surface microchannels, or other suitable materials or features that help form a volume-reduced pathway between sweat glands and sensors.

Figure 3:
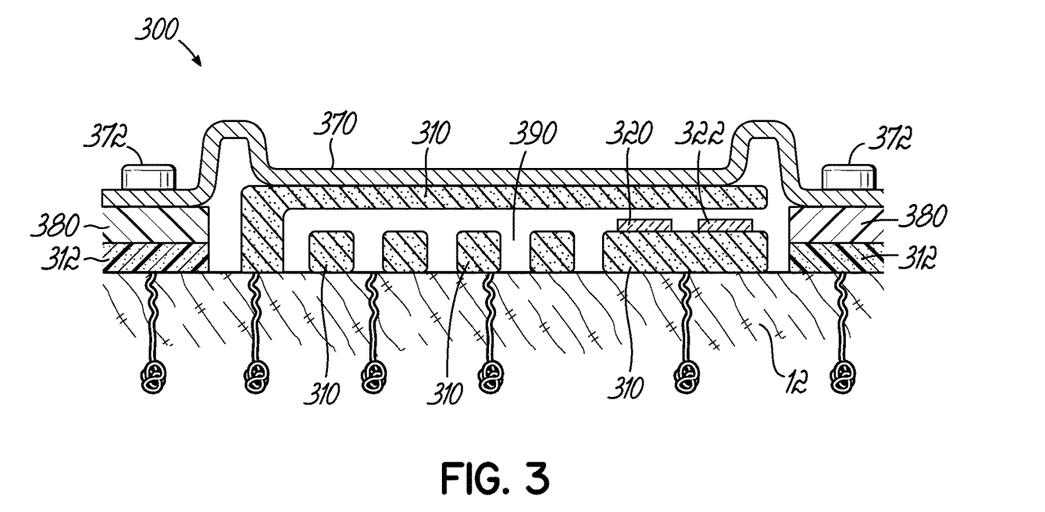
FIG. 3 is a cross-sectional view of a portion of a device for sweat biosensing with a reduced microfluidic volume according to another embodiment.

With reference to FIG. 3, in an embodiment, a device 300 is placed on the skin 12 and creates a reduced sweat volume. In this embodiment, pressure is applied to a rigid polymer sweat collector 310 by a flexible metal clamp 370 coupled to a rigid printed circuit board 380 that is adhered to skin by adhesive 312. The flexible metal clamp 370 may be coupled to the rigid printed circuit board 380 via fasteners, such as bolts 372. In other embodiments, a metal spring, fluid filled bag, or other form of a pressure element could be used beneath a rigid metal clamp (not shown). Generally, to allow reliable pressure in an embodiment where an adhesive is used for holding the device 300 against skin 12, the contact area of the adhesive with the skin 12 should be at least 3× greater than the contact area of the sweat collector with skin 12 and, more preferably, 10× greater.

Figure 4:
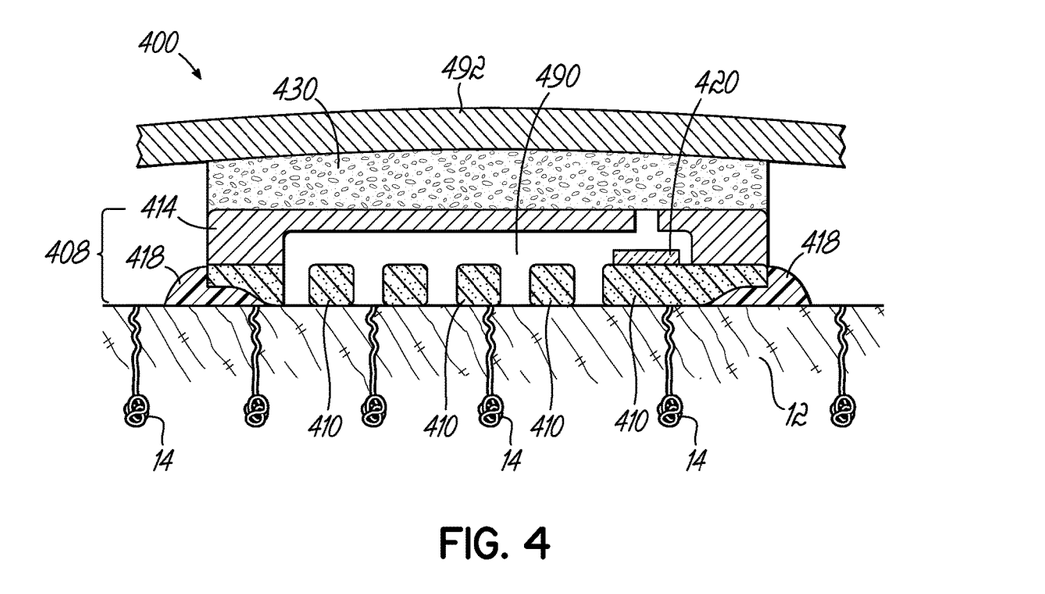
FIG. 4 is a cross-sectional view of a portion of a device for sweat biosensing with a reduced microfluidic volume according to another embodiment.

With reference to FIG. 4, in an embodiment of the disclosed invention, a device 400 is secured against the skin 12 by a strap 492, such as a wrist-band. The device 400 further includes a wicking pump 430, which absorbs excess sweat from the sweat collector 408. The sweat collector 408 is comprised of a rigid portion 414, such as glass, which helps provide uniform pressure against the skin 12, and a bonded portion 410 that can be, for example, a flexible siloxane polymer, which helps the device 400 conform against the skin 12. A sensor 420 is contained within the sweat collector 408. The device 400 further includes a sweat impermeable non-solid material 418, such as a cosmetic oil, petroleum jelly, or a water-proof medical adhesive. The sweat impermeable material 418 seals the sweat collector 408 against skin 12 so that sweat does not leak beyond the periphery of contact of the sweat collector 408 with the skin 12. Therefore, sweat is forced by pressure into the sweat collector 408 and the space 490 and towards the sensor 420. In an embodiment, the space 490 may be suitably hydrophilic (e.g., an oxygen plasma treated surface) so that its wicking characteristic aids in pulling sweat into the device 400.

Figure 5:
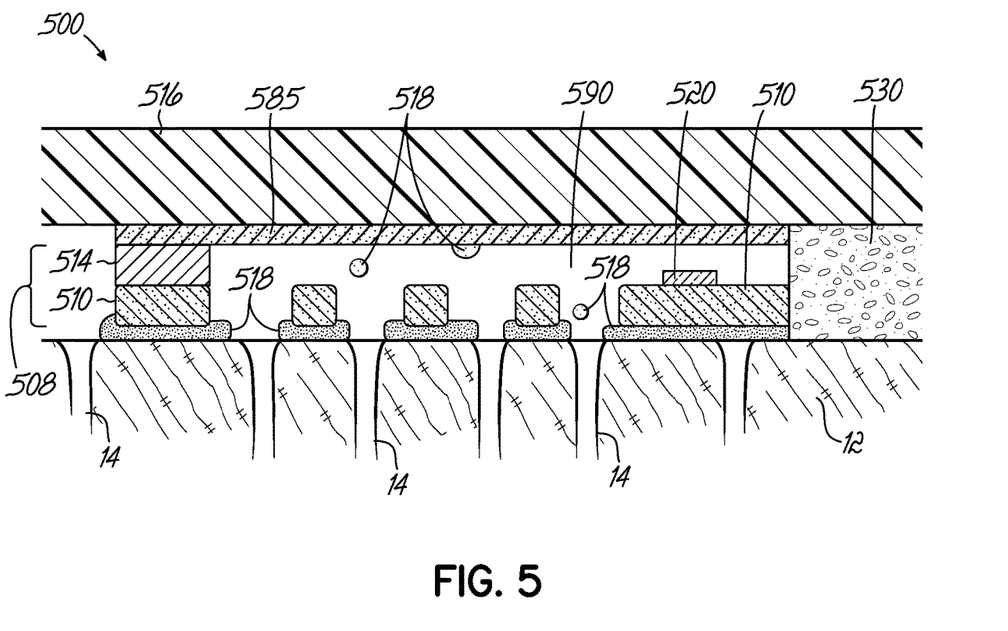
FIG. 5 is a cross-sectional view of a portion of a device for sweat biosensing with a reduced microfluidic volume according to another embodiment.

With reference to FIG. 5, in an embodiment, a device 500 is secured against the skin 12 with pressure by aid of a plastic housing 516 that is part of a larger component (not shown). The device 500 further includes a sweat impermeable non-solid material 518 positioned between the sweat collector 508 and the skin 12. The sweat impermeable non-solid material 518 could be, for example, a low-surface tension fluid, gel, a paste, or a cosmetic oil or petroleum jelly. This material 518 aids sealing of the sweat collector 508 against the skin 12 so that the seal is more water and pressure tight. However, if the material 518 is oily, the oil could come loose from the device 500 or skin surface and, if it reaches the sensor 520, could foul said sensor 520 and render it inoperable. Similarly, if the oily material 518 reaches the wicking pump 530, it could occlude the pores of the wicking pump 530 as well and render it inoperable. Therefore, the device 500 includes an oleoscopic material 585 that captures oily material 518 and that could also capture natural oil from the skin 12. Other embodiments could include an oleoscopic material as well (not shown) for capturing natural oil from the skin surface. The oleoscopic material 585 could be, for example, a Teflon membrane or an oleoscopic polymer such as those used commercially for oil-spill cleanup.

With further reference to FIG. 5, in an alternate embodiment of the disclosed invention, the sweat collector 508 of a device 500 is comprised of two laminated plastic materials 510, 514. Pressure to secure the sweat collector 508 against the skin 12 could be achieved by application of a vacuum, and for example, element 530 could be a vacuum providing component that could enable the previously taught pressure ranges for securing a sweat collector 508 against the skin 12. The vacuum providing component may be, for example, a miniature vacuum pump, a vacuum piston, a vacuum reservoir with a pressure regulator, or other suitable vacuum elements. Sweat impermeable non-solid material 518 is important to help maintain proper vacuum against skin 12, and, due to the vacuum, the material 518 may be highly viscous and possibly gel-like or paste-like (i.e., not flowing as a Newtonian fluid) such that material 518 is not sucked into the vacuum to a degree at which the device would fail (e.g. clogged with material 518, sensors fouled by material 518, or vacuum seal with skin breached because of a lack of material 518). The vacuum providing component could have a suitable volume such that sweat could also be pulled into the vacuum providing component. Alternately, the material 518 could be replaced by an adhesive material if it achieves the same vacuum seal against skin. Generally, an adhesive, material 518, or other suitable material may be referred to as a vacuum sealing material on the skin 12. Vacuum providing components could also provide a pressure that is communicated to the skin surface not by air, but at least in part by fluid (e.g. the same elements above but pulling sweat under negative pressure relative to the body). Alternately, a very strongly wicking or drawing material could pull sweat and, therefore, provide a negative pressure to pull the skin against the sweat collector. Such a component that applies pressure according to the disclosed invention by providing a negative pressure on fluid in the device may be more specifically referred to as a negative fluid pressure providing component.

Figure 6:
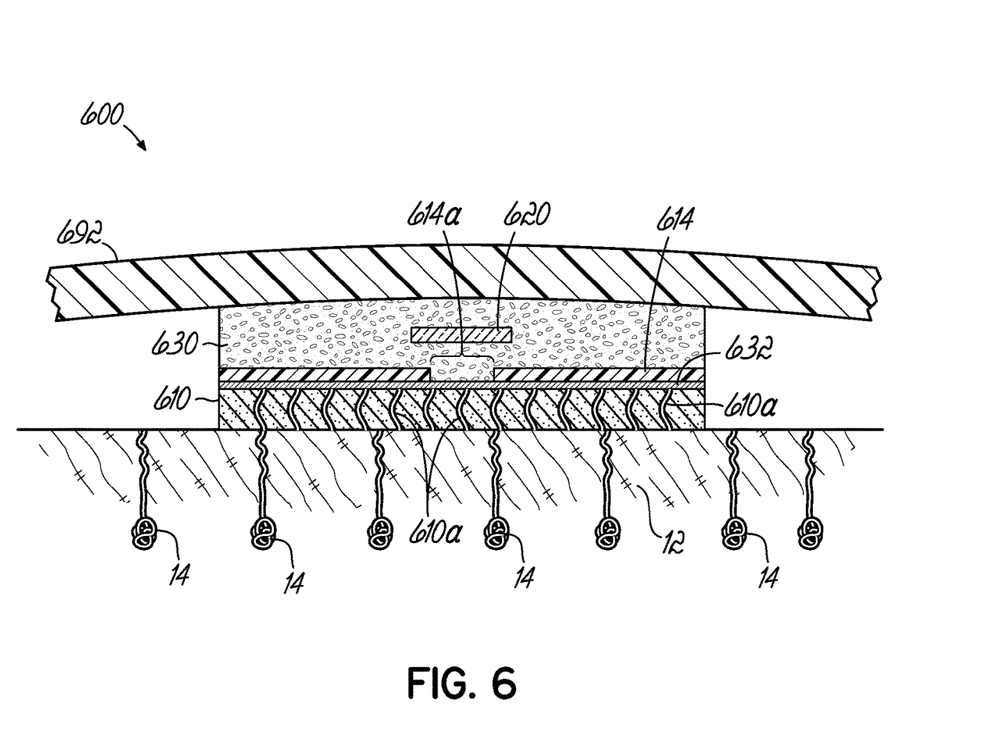
FIG. 6 is a cross-sectional view of a portion of a device for sweat biosensing with a reduced microfluidic volume according to another embodiment.

With reference to FIG. 6, in an embodiment of the disclosed invention, a device 600 includes a sensor 620 embedded in a wicking component, such as a hydrogel 630. A sweat impermeable layer, such as a polymer 614, is positioned between the hydrogel 630 and a wicking layer, such as a cellulose layer 632. The hydrogel 630 contacts a portion of the cellulose layer 632 through an aperture 614a in the polymer 614. The cellulose layer 632 is positioned between the polymer 614 and a flexible or rubbery polymer 610, such as latex, that includes incompressible pores 610a. Incompressible pores 610a could be, for example, fibers, semi-rigid polymer tubes, or other features that allow the polymer 610 to mold itself against the skin 12, hair, defects, etc., while the pores 610a do not collapse (and therefore can continue to bring sweat from skin 12 into the polymer 610, through the cellulose layer 632, and into the hydrogel 630). The device 600 is secured against the skin 12, for example, by an inner lining of a helmet 692 so that, for example, the sweat collector 610 could therefore be held on a forehead.

Figure 7A:
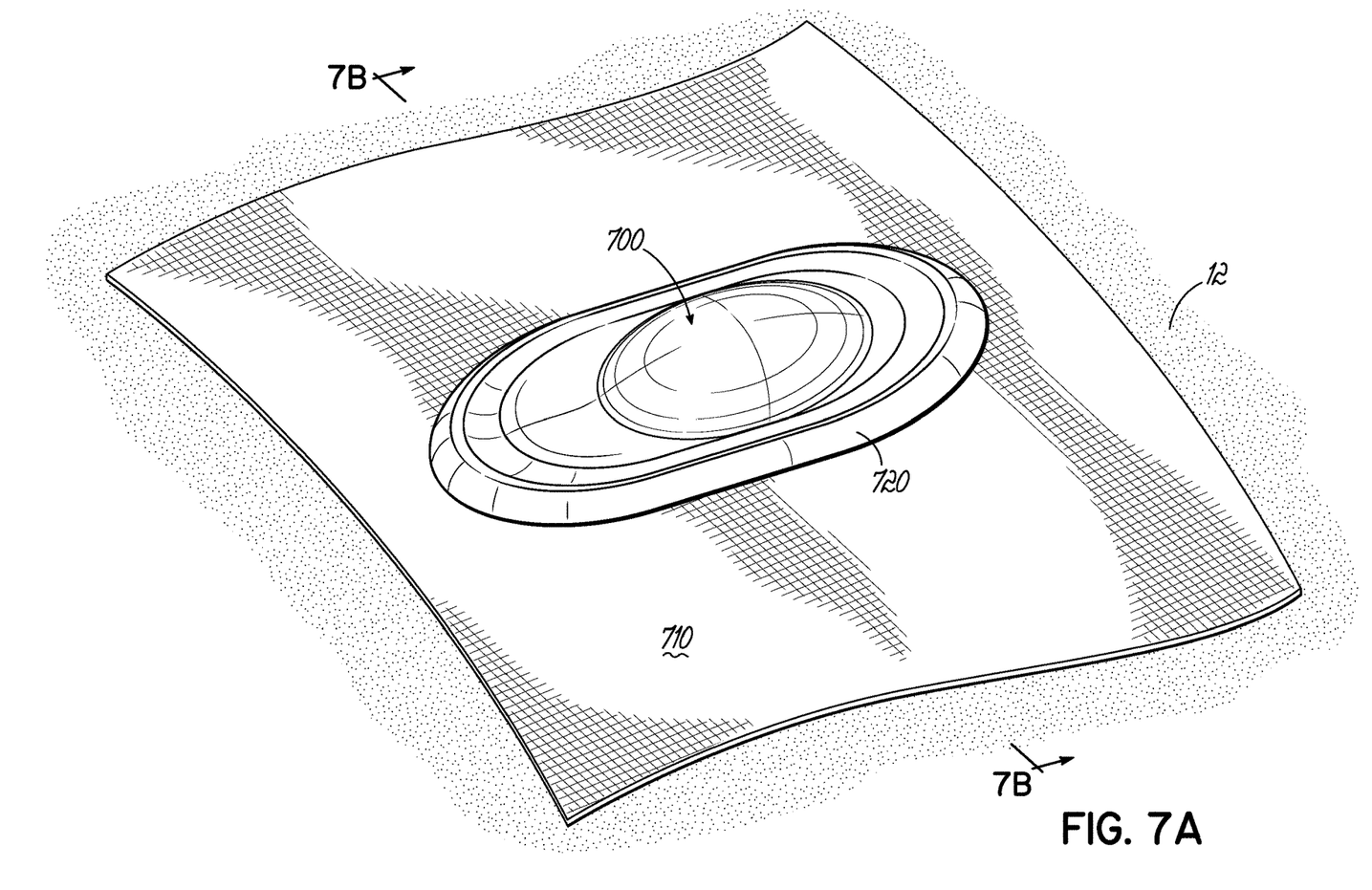
FIG. 7A is a perspective view of a portion of a device for sweat biosensing with a reduced microfluidic volume and flexible collar according to another embodiment.
Figure 7B:
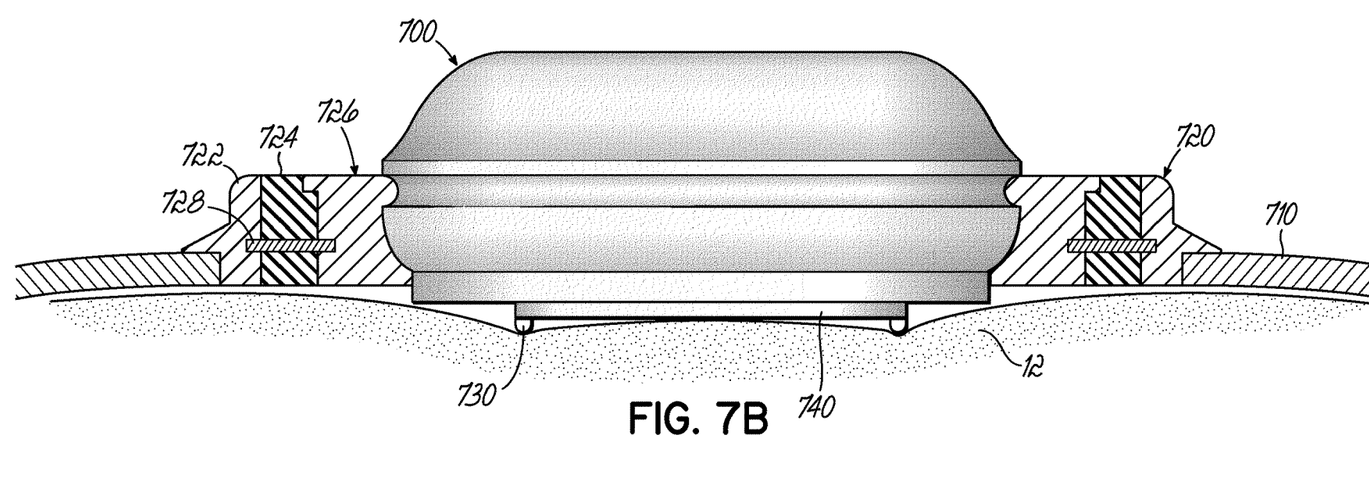
FIGS. 7B and 7C are partial cross sectional views of the device generally taken along the line 7B-7B of FIG. 7A.
Figure 7C:
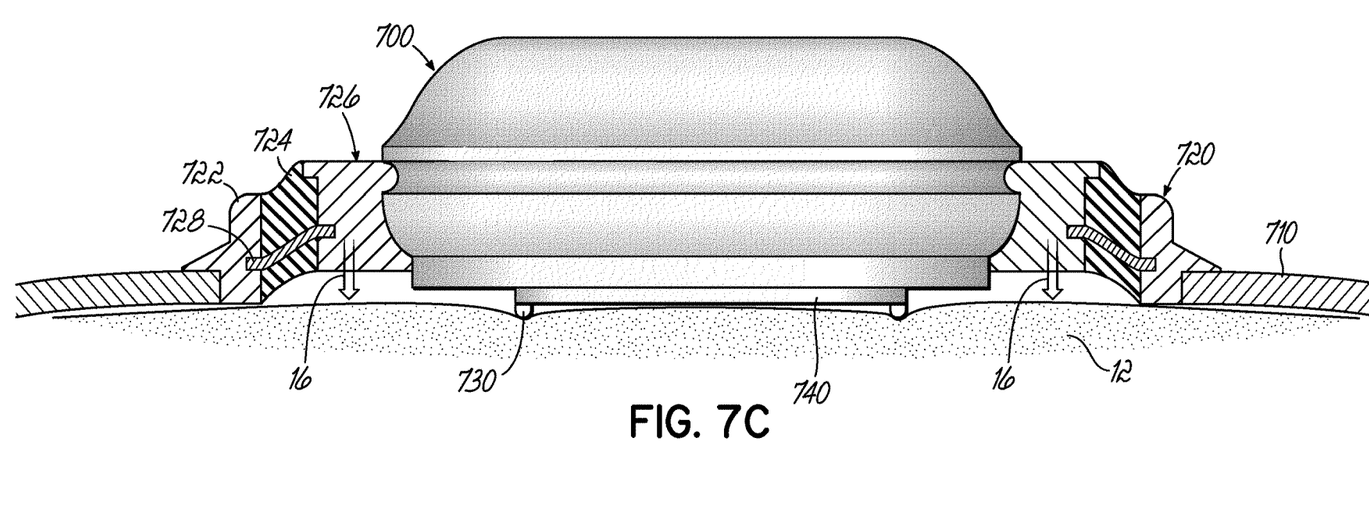

With reference to FIGS. 7A-7C, in an embodiment of the disclosed invention, a device 700 is depicted that is configured to minimize pressure variations on the device 700 as it is worn on the skin 12. The device 700 includes a sweat collector 740 that interfaces with a known area of the skin 12, and includes a seal 730 that is configured to prevent sweat generated by the skin 12 within the collection area from escaping and to prevent sweat generated outside of the seal 730 from entering the collection area. Although not shown, the device 700 includes components for collecting and sensing sweat as described above. The device 700 is secured to the skin 12 by means of a stretchable strap or band 710. Suitable materials for the stretchable strap or band 710 includes a vinyl or nylon strap, spandex sleeve, textile elastic band, etc. While donning the device 700, a user will apply varying initial pressures to the device 700 from day to day. The initial pressure applied by the user is affected by various factors such as the user's changing comfort preferences, or the degradation of the elasticity of the strap 710 over time. Additionally, during use, the device 700 will see pressure variations caused by user movement, or device 700 interaction with clothing or other external environmental factors. Therefore, the device 700 includes a flexible mechanism attaching the device 700 to the strap 710 to maintain a consistent pressure on the device 700.

With reference to FIGS. 7B and 7C, the device 700 interacts with the attachment strap 710 by means of a flexible collar 720. The device 700 is removably snapped into the flexible collar 720 for use, and is snapped out of the flexible collar 720 upon completion of use. In other words, the device 700 is removably coupled to the strap 710 via the flexible collar 720. The flexible collar 720 comprises one or more sections 722, 724, 726 that allow the device 700 to flex within the strap 710 so that the pressure of the device 700 against the skin 12 is substantially decoupled from the tightness of the strap 710 against the device 700. While three sections 722, 724, 726 are depicted, it should be recognized that the number of sections may be one, two, or more than three. For example, a first section 722 is coupled to the strap 710, and a third section 726 is removably coupled to the device 700. The second section 724 is coupled to the other sections 722, 726 and flexes to allow motion therebetween. Suitable materials for the section(s) 722, 724, 726 include high density foam, textiles, such as neoprene, or other suitable material. The section(s) 722, 724, 726 can be of different densities or rigidities so that the combination of section(s) 722, 724, 726 provides a substantially constant pressure between the device 700 and the skin 12 that is substantially independent from variations in pressure from the strap 710 on the device 700. Such pressure supplied by the flexible collar 720 will remain constant despite increasing deflection of the device 700 from the neutral position. The pressure by the flexible collar 720 is constant, rather than increasing with additional deflection (which would be a linear or geometric force). So, the pressure put on the device 700 by the flexible collar 720 is the same back to neutral, regardless of the amount of deflection. This has a dampening or decoupling effect between the strap 710 and the device 700. In an embodiment, the flexible collar 720 includes an additional component to provide structure to the flexible collar 720, such as a plurality of suspension wires or springs 728 that apply a constant force to the device 700 when the suspension wires 728 are deflected from their initial position. Suitable materials for the suspension wires 728 include metal, metal alloys, such as steel, or superelastic metal alloys, such as nickel titanium (nitinol). Suspension wires 728 made from a superelastic alloy can apply a constant pressure to the device 700, since the superelastic properties of the metal allow the wires 728 to flex but tend to return to a neutral state as soon as external pressure is removed. With reference to FIG. 7C, if the device 700 is deflected up relative to the strap 710, the flexible collar 720 puts a constant downward force (arrows 16) on the device 700 to maintain a constant pressure against the skin 12. In the illustrated embodiment, the position of the suspension wires 728 move between an initial, relaxed state as shown in FIG. 7B and a second, deformed state as shown in FIG. 7C. The resilient properties of the suspension wires 728 cause at least a portion of the downward force on the device 700 as the deformed suspension wires 728 strain to return to the initial, relaxed state. As shown, the section 724 may be of a different density or rigidity compared to sections 722, 726 such that it flexes as the device 700 is deflected away from the skin 12.

Figure 8A:
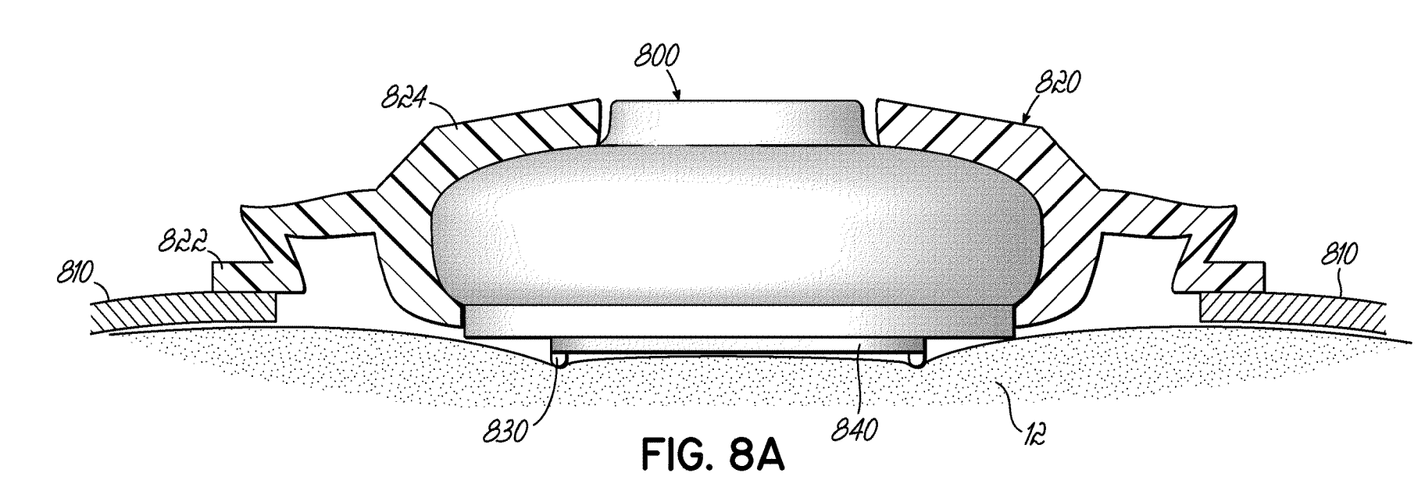
FIGS. 8A and 8B are cross sectional views of a portion of a device for sweat biosensing with a reduced microfluidic volume and flexible collar according to another embodiment.
Figure 8B:
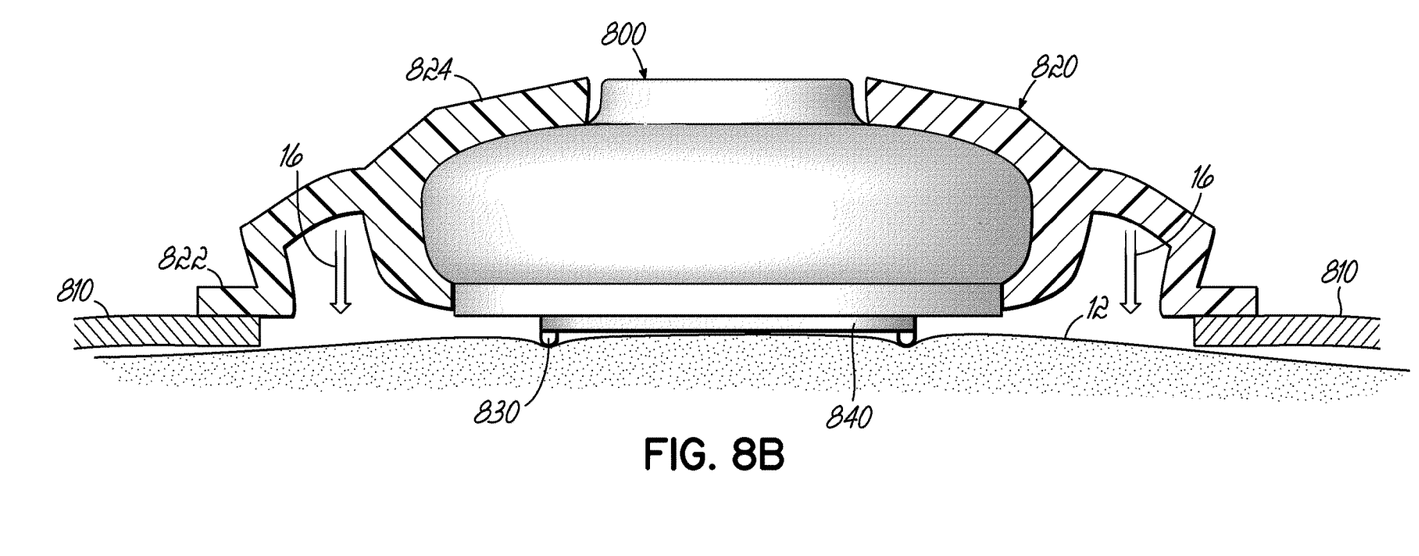

With reference to FIGS. 8A and 8B, in another embodiment of the disclosed invention, an elastomeric bellows 820 holds a device 800 in substantially constant pressure against the skin 12, while allowing the strap 810 to move flexibly. The elastomeric bellows 820 is constructed of, for example, nylon, an elastomer, such as a thermoplastic elastomer (TPE), or another suitable material, and is configured to act as a spring that puts a substantially constant force on the device 800 when the elastomeric bellows 820 is flexed away from its neutral position. The elastomeric bellows 820 has an outer rim 822 that is secured to or integrated into the strap 810, and an inner rim 824 that is removably attached to the device 800, so that the device 800 can be snapped into place for use and snapped out of the strap 810 for removal. In an embodiment, the elastomeric bellows 820 is overmolded (not shown) onto the strap 810 to improve the integrity and ease of manufacture of the device 800.

The following examples are provided to help illustrate the disclosed invention, and are not comprehensive or limiting in any manner.

Example 1

A wicking collector area of 0.1 cm² positioned on skin with an active sweat gland density of 100 glands/cm² translates to 10 glands facing the wicking collector. A sweat generation rate of 0.5 nL/min/gland translates to a total sweat flow rate to the collector of about 5 nL/min. It should be recognized that this example can be adapted to other gland densities, sweat generation rates, wicking collector areas, skin roughness, or alternate use scenarios or device designs.

Consider now the device 100 of FIG. 1A and/or the device 300 of FIG. 3. In an embodiment, the sweat collector is constructed of multi-layer SU-8 polymer, which has a water contact angle of 90 degrees. The internal surfaces of the sweat collector are coated with 10 nm of poly-vinyl-alcohol or sucrose to be initially superhydrophilic to sweat. The SU-8 polymer collector (e.g., sweat collector 110) is adjacent to the skin and is 20 μm thick. The SU-8 polymer collector includes pores that open into a 10 μm thick channel. The sweat volume (e.g., sweat volume 190) includes the open space of the pores and the open space of the channel in the sweat collector. The pores have an aspect ratio of about 1:1 and comprise 5% of the 0.1 $cm^2$ area of the polymer. The portion of a sweat volume for the pores would be 0.1 $cm^2$*20E-4 cm*0.05=1E-5 $cm^3$=1E-5 mL=10 nL. The channel includes supports (e.g., spacer beads or posts; not shown) that transfer pressure toward the skin and that comprise 10% of the channel volume. Thus, the remaining sweat volume portion would have 0.1 $cm^2$*10E-4 cm*0.9=90 nL. At 5 nL/min, the sweat sampling interval would be roughly 18 minutes based on a simple volume-filling approach. If the thickness of the polymer was 40 μm and the thickness of the channel was 20 μm (doubled), then the sweat sampling interval would be 36 minutes. If the thicknesses above were 80 μm and 40 μm (quadrupled), respectively, then the sweat sampling interval would be 72 minutes (greater than 1 hour roughly).

Example 2

Consider a use scenario similar to Example 1 described above and the device 400 of FIG. 4 where a thickness of the hydrogel 430 is 10 μm, and the sensor(s) 420 has a total area of 0.01 $cm^2$. The portion of a sweat volume for hydrogel 430 would therefore be 10 nL. Assume the wicking cellulose layer 432 is 5 μm thick (nano-cellulose) and 40% solids, so that its portion of the sweat volume is 20 nL. Lastly, assume incompressible pores 610*a* are only several microns or less in diameter and no more than 30 μm long, so that their contribution to the total sweat volume is negligible. As a result, a total sweat volume is near 30 nL, and the sweat sampling interval could be 6 minutes.

While specific embodiments have been described in considerable detail to illustrate the disclosed invention, the description is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of the general inventive concept.

What is claimed is:

1. A sweat sampling and sensing device for sensing sweat on skin comprising:
    an analyte-specific sensor for sensing a first analyte in sweat;
    a sweat collector adapted to be placed on or adjacent to the skin with one or more pores or pathways for entry of sweat from the skin into said sweat collector, said sweat collector at least partly defining a sweat volume between said analyte-specific sensor and the skin; and
    a pressure element capable of holding said sweat collector against the skin with a pressure and reducing the sweat volume between said sweat collector and the skin;
    wherein the pressure element comprises an adhesive that has a contact area with skin that is at least 3× greater than a contact area of the sweat collector with skin, and the pressure is in a range of at least 60 $N/m^2$ and less than 40,000 $N/m^2$.

2. The device of claim 1, wherein said pressure element comprises at least one of: an adhesive; a memory foam; a sponge; a mechanical clamp; a spring; a fluid filled bag; a gel; a hydrogel; a strap; a plastic housing; a vacuum providing component; or a negative fluid pressure providing component.

3. The device of claim 1, wherein said pressure element comprises at least in part an adhesive that has 10× greater contact with skin than contact area of said sweat collector.

4. The device of claim 1, further comprising a sweat-impermeable non-solid material coating on said sweat collector.

5. The device of claim 4, wherein said sweat-impermeable non-solid material is an oil.

6. The device of claim 4, wherein said sweat-impermeable non-solid material is a gel.

7. The device of claim 4, wherein said sweat-impermeable non-solid material is an adhesive.

8. The device of claim 4, wherein said sweat-impermeable non-solid material is a paste.

9. The device of claim 1, wherein said one or more pores or pathways are incompressible.

10. The device of claim 1, further comprising an oleoscopic material.

11. The device of claim 1, further comprising a vacuum providing component and a vacuum sealing material adapted to be placed on skin.

12. The device of claim 1, further comprising a negative fluid pressure providing component and a vacuum sealing material adapted to be placed on skin.

13. The device of claim 1, wherein the pressure element is configured to hold the device against the skin with a substantially constant pressure, wherein the pressure element compensates for pressure variabilities due to initial donning variations, and due to motion while the device is in use.

14. The device of claim 13, wherein the pressure element comprises one of the following: an elastomeric bellows, a flexible suspension collar, or a fabric decoupler.

15. The device of claim 14, wherein the pressure element comprises the flexible suspension collar, the flexible suspension collar comprising a plurality of sections, at least one of the plurality of sections having a different density than the other sections.

16. The device of claim 14, wherein the pressure element comprises the flexible suspension collar, the flexible suspension collar comprising a plurality of wires made from a superelastic metal alloy.

17. The device of claim 14, wherein the pressure element comprises the flexible suspension collar, the flexible suspension collar comprising a plurality of wires made from spring steel.

18. The device of claim 1, further comprising a flexible seal tracing the sweat collector's path of contact with the skin, where the pressure element is configured to apply sufficient pressure between the seal and the skin to prevent sweat from entering the collection area from outside the seal.

19. The device of claim 1, wherein said analyte-specific sensor is positioned on an interior surface of the sweat collector.

* * * * *